United States Patent [19]

Otten

[11] Patent Number: 5,480,421
[45] Date of Patent: Jan. 2, 1996

[54] LEAD WITH STYLET CAPTURE MEMBER

[75] Inventor: Lynn M. Otten, Blaine, Minn.

[73] Assignee: Medtronic, Inc., Minneapolis, Minn.

[21] Appl. No.: 286,739

[22] Filed: Aug. 5, 1994

Related U.S. Application Data

[63] Continuation of Ser. No. 969,620, Oct. 30, 1992, Pat. No. 5,360,441.

[51] Int. Cl.$^6$ .................................................... A61N 1/372
[52] U.S. Cl. ............................................ 607/122; 607/116
[58] Field of Search ............................ 128/639, 642, 128/772; 607/115–118, 122, 125–128, 130–132; 604/164–166, 280

[56] References Cited

U.S. PATENT DOCUMENTS

| | | |
|---|---|---|
| 3,902,501 | 9/1975 | Citron et al. . |
| 4,285,347 | 8/1981 | Hess . |
| 4,419,819 | 12/1983 | Dickhudt et al. . |
| 4,498,482 | 2/1985 | Williams . |
| 4,548,206 | 10/1985 | Osborne ................................ 128/772 |
| 4,913,164 | 4/1990 | Greene et al. . |
| 4,920,980 | 5/1990 | Jackowski ........................... 128/658 X |
| 4,932,419 | 6/1990 | De Toledo ............................ 128/772 |
| 4,957,118 | 9/1990 | Erlebacher . |
| 5,003,992 | 4/1991 | Holleman et al. .................. 128/642 X |
| 5,109,867 | 5/1992 | Twyford, Jr. ............................ 128/772 |

*Primary Examiner*—Angela D. Sykes
*Attorney, Agent, or Firm*—Curtis D. Kinghorn; Harold R. Patton

[57] ABSTRACT

A lead having a capture member for releasably engaging the enlarged distal tip of a stylet. The capture member is connected to the flexible tubular casing of the lead near the distal end and includes an aperture having a necked down portion and a socket portion. The socket portion is shaped to accomodate the enlarged distal tip of the styler. As the stylet is advanced towards the distal end of the lead the enlarged tip enters the necked down portion and is directed towards the socket portion until it pops into and is engaged within the socket portion. Once engaged the lead can be advanced, partially withdrawn, or turned by manipulating the stylet handle.

8 Claims, 1 Drawing Sheet

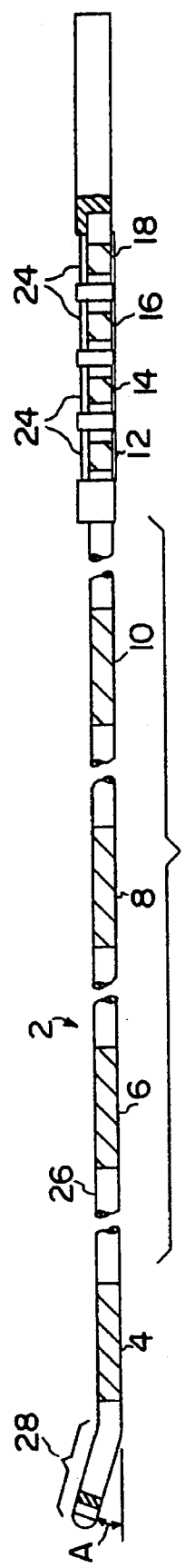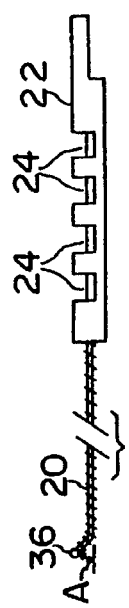

LEAD WITH STYLET CAPTURE MEMBER

This is a continuation of U.S. Pat. No. 5,360,441, issued Nov. 1, 1994, Ser. No. 969,620, filed Oct. 30, 1992.

Reference is made to our co-pending application, Ser. No. 07/969,600, filed on even date herewith entitled CATHETER WITH RETRACTABLE ANCHOR MECHANISM, which is hereby incorporated by reference.

FIELD OF THE INVENTION

This invention relates to leads capable of delivery of electrical stimulation to body tissue and which utilize a stylet for steering and positioning the lead. More particularly, the invention is directed to an improved lead having a capture member for releasably engaging the enlarged distal tip of a stylet for providing enhanced control in guiding the lead to the desired location.

BACKGROUND OF THE INVENTION

The state of the art of implantable pulse generators for stimulating human tissue has advanced to the point that such devices are being designed and used in increasing numbers to treat a wide variety of medical conditions. In addition to implantable pulse generators for treating many different types of cardiac conditions (bradycardia, tachycardia, fibrillation, and the like), so-called neurological pulse generators have been provided for stimulating a patient's nervous system, in order to treat such diverse conditions as pain, motor impairment, incontinence, and impotence, to name only a few.

In most cases, electrical stimulation pulses are conveyed from an implanted pulse generator to the desired stimulation site by means of an implanted lead having exposed electrodes at its distal end. In order to achieve the desired effects from delivery of stimulating pulses it is of course very important that the lead be properly positioned and stabilized in the patient, so that as much of the stimulating energy as possible is delivered to the appropriate site. While this is true for all kinds of stimulation pulse therapies, lead positioning is especially critical in the area of neurological pacing, such as when stimulation pulses are delivered by a lead positioned in the epidural space adjoining the patient's spinal column. The delicate and highly sensitive nature of the spinal column, and the possible harmful or otherwise undesirable effects of delivering stimulation pulses to an inappropriate site in this area accentuates the need for accurate control in the guidance and positioning of the lead in order to achieve precise lead placement.

Stylets are commonly used in the field of neurological stimulation as a means for guiding and properly placing leads. Examples are disclosed in U.S. Pat. Nos. 4,285,347 to Hess and 4,419,819 to Dickhudt et al. Disclosed are neurological leads which utilize stiff wired stylets which provide the stability to the lead which is necessary to enable the lead to be inserted into the body through a Touhy needle and be guided in the body to the area of desired placement. In both cases the stylets are also used to retract anchor or stabilizing mechanisms while the lead is being inserted. In both leads the stylet is freely moveable within the lead at all times. Thus, although advancement of the stylet may advance the lead, withdrawal of the stylet does not result in a similar withdrawal of the lead.

Neurological leads which utilize stylets for guidance are also subject to the problem of lead twisting or torquing during placement. When the lead is being implanted it is common to use a stylet which is bent at an angle at the distal end in order to impart a similar bend to the distal end of the lead. Such a bend allows the lead to be manipulated around curves or corners. However, when these curves or corners are negotiated it may be necessary to rotate the lead. This can result in the lead rotating with respect to the stylet and creating rotational forces (torque). This creates a problem since, at some point, these forces will be released resulting in the lead twisting back to its normal position and quite possibly mis-aligning the lead.

In the field of cardiac pacing leads the use of stylets to guide the lead through a vessel to the inside of the heart is well known and very important to the proper placement of the lead. An example of such a lead is disclosed in U.S. Pat. No. 3,902,501 to Citron et al. In this lead the stylet is also used to release tines at the distal end in order to anchor the lead. In U.S. Pat. No. 4,913,164 to Greene et al. a pacing lead is disclosed in which a stylet is used to engage tines to anchor the lead. In one embodiment the distal end of the stylet may be threaded into an internal cup which allows a plunger to be drawn back by the stylet which results in the tines being withdrawn. U.S. Pat. No. 4,957,118 to Erlbacher discloses a pacemaker lead with an actuating rod permanently inserted in the lumen of the lead. The actuating rod is used to actuate tines at the distal end of the lead and also to conduct electrical signals to the tip of the lead. There is no provision in any of these leads for the use of a stylet for manipulating the insertion, positioning or withdrawal of the lead.

In U.S. Pat. No. 4,498,482 to Williams a transvenous pacing lead having a stylet with a ball shaped distal tip is disclosed. The tip of the stylet is soft for the purpose of allowing it to comply with curvatures and bends in the pacing lead. A similar ball tipped stylet is disclosed in U.S. Pat. No. 5,003,992 to Holleman et al. In the lead disclosed the ball tip of the stylet is inserted past a retainer ring in order to engage the stylet and allow the stylet to advance or retract an electrode at the distal tip of the lead. The stylet is used during placement of the lead only to keep the distal electrode retracted.

The problem with these leads is that they provide for use of the stylet only to stiffen the lead during its advancement. The stylet is not fixed with respect to the lead body to allow the stylet to be used to control lead advancement or retraction used in optimizing the position of the lead. These leads also make no provision for solving the problem of lead torquing.

In order to overcome the problems associated with present leads as set forth above it can thus be seen that there is a need for a lead having a stylet which is releasably secured with respect to the body of the lead. This provides the stylet with enhanced control during placement of the lead and stabilizes the lead body with respect to the stylet to overcome the problem of torquing.

SUMMARY OF THE INVENTION

In accordance with the present invention, a lead having a distal end and a proximal end for insertion in the human body is provided. The lead has a flexible tubular outer casing which is substantially concentric to the longitudinal axis of the lead and defines a central lumen. A stylet having an enlarged tip of predetermined shape at its distal end is provided for insertion in the central lumen. The stylet is releasably received in a capture means which is connected to the tubular casing. The capture means comprises a capture member which has an aperture with a necked down portion and a socket portion. The socket portion is shaped to accommodate the predetermined shape of the distal end of the styler.

The lead may include at least one electrode located near the distal end and at least one conductor for transmitting electrical signals from the proximal end of the lead to the electrode.

In one embodiment the invention comprises an epidural lead having a distal end and a proximal end. The epidural lead has a flexible tubular outer member which is substantially concentric to the longitudinal axis of the lead, the outer member extending substantially the entire length of the lead. A flexible tubular inner member is provided and which lays within said outer member, the inner member having a distal end located near the distal end of the lead. The inner member extends substantially to the proximal end of the lead and defines a central lumen. The lead has at least one electrode secured to the outer member near the distal end of the lead and includes at least one conductor connected to the electrode for transmitting electrical signals from the proximal end of the lead to the electrode. A stylet is provided for insertion in the central lumen of the lead, the stylet having an enlarged tip at its distal end. The lead includes capture means which is connected to the flexible tubular outer member for releasably receiving the enlarged tip of the stylet so that the catheter may be positioned at the desired location by advancing or withdrawing the stylet.

BRIEF DESCRIPTION OF THE DRAWINGS

The foregoing and other aspects of the present invention will be best appreciated with reference to the detailed description of the invention, which follows, when read in conjunction with the accompanying drawings wherein:

FIG. 1 is an illustration of a lead in accordance with one embodiment of the present invention;

FIG. 2 is a partially cut-away top view of the distal end of the lead of FIG. 1;

FIG. 3 is a partially cut-away side view of the distal end of the lead of FIG. 1; and FIG. 4 is an illustration of the stylet in accordance with the present invention.

DETAILED DESCRIPTION OF THE INVENTION

In FIG. 1 there is shown a lead 2 in accordance with the present invention. Lead 2 is provided with one or more electrodes 4, 6, 8 and 10 which are connected by conductors (not shown) in a conventional manner to contacts 12, 14, 16 and 18 located at the proximal end of lead 2. Lead 2 may be constructed similar to neurological stimulation leads marketed by Medtronic, Inc., and identified as model numbers 3885, 3888, 3487T and 3487A.

In FIG. 4 a stylet 20 in accordance with the present invention is illustrated. Stylet 20 is connected to stylet handle 22. Stylet 20 is a stiff wire stylet which may be generally straight or may, as shown, be angled at the distal end at some angle A as measured from the longitudinal axis of the stylet. Angle A is preferably an acute angle of from 0 to 15 degrees. Stylet handle 22 is provided with a plurality of openings 24 which are positioned such that when stylet 20 is fully inserted into lead 2 contacts 12, 14, 16 and 18 are exposed through openings 24 as shown in FIG. 1. This allows contacts 12, 14, 16 and 18 to be temporarily connected to an external stimulator such as, for example, a Medtronic Model 3625 Neurological screener while the stylet is inserted. After the optimum placement of the lead is determined the stylet is removed and the lead is connected to an implanted receiver or pulse generator such as the Medtronic Itrel series stimulation systems for long term nerve or muscle stimulation.

With reference again to FIG. 1, the exterior of lead 2 consists of a flexible tubular outer casing 26. When the lead is fully inserted the distal end 28 is bent from the longitudinal axis of the lead at an angle A corresponding to the angle at which the stylet is bent.

With reference to FIGS. 2 and 3 which are partially cut away top and side views, respectively, of the distal end of lead 2 the engagement of stylet 20 at the distal end of the lead can be explained. Flexible tubular outer casing 26 preferably consists of an outer tubular member 30 and an inner tubular member 32. Tubular members 30 and 32 maybe comprised of polyurethane, silicone rubber or other biologically compatible polymer of sufficient memory retentive characteristics. The inner surface of inner tubular member 32 defines a central lumen 34 through which stylet 20 is inserted. Stylet 20 has an enlarged tip 36 of predetermined shape at its distal end. A capture member 38 is positioned in the distal end 28 of lead 2 and is secured to the inner surface of outer tubular member 30. Capture member 38 includes an aperture 40 having a necked down portion 42 and a socket portion 44. Socket portion 44 is shaped to accommodate the enlarged tip 36 of stylet 20.

The operation of capture member 38 can be described as follows. As stylet 20 is advanced towards distal end 28, enlarged tip 36 enters necked down portion 42 and is directed towards socket portion 44. Continued advancement of stylet 20 results in enlarged tip 36 being fitted or popped into socket portion 44. An advantage of this construction is that the physician tactiley feels the releasable engagement and disengagement of styler tip 36 as it pops into and out of socket portion 44.

Once enlarged tip 36 is received within socket portion 44 the lead may be implanted. If the lead is of the epidural lead type such as in this embodiment of the present invention, the lead is generally implanted in the body by inserting it though a Touhy needle. In most prior art leads the stylet is inserted in the central lumen and stops at the closed distal end of the lead body. By utilizing the present invention, however, the distal tip of the stylet is releasably engaged at the distal end of the lead. This provides the physician with increased control of lead positioning. By utilizing the stylet handle the lead can be advanced, partially withdrawn, or turned simply by manipulating the stylet handle. The engagement of the distal end of the stylet is such that the angular configuration of the distal end 28 is stabilized thus enhancing steerability. The problem of torquing is also virtually eliminated since the lead is no longer free to rotate with respect to the stylet.

From the forgoing detailed description of specific embodiments of the invention, it should be apparent that a lead with a capture member for releasably engaging the distal end of a stylet has been disclosed. Although a particular embodiment of the invention has been disclosed herein in detail, this has been done for the purpose of illustration only, and is not intended to be limiting with respect to the scope of the appended claims, which follow. In particular, it is contemplated by the inventor that various substitutions, alterations and modifications may be made to the embodiments of the invention described herein without departing from the spirit and scope of the invention as defined by the claims. For instance, the choice of materials or variations of the shape of the capture mechanism, or the distal tip of the stylet are believed to be a matter of routine for a person of ordinary skill in the art with knowledge of the embodiments disclosed herein. Likewise, although the embodiments disclosed relate primarily to epidural leads for spinal cord stimulation, the present invention could be used for other applications such as cardiac pacing leads or catheters for the delivery of or withdrawal of fluids from the body.

I claim:

1. An epidural lead having a distal end and a proximal end, the epidural lead comprising:

a flexible tubular outer member substantially concentric to a longitudinal axis of the lead, said outer member extending substantially an entire length of the lead, a flexible tubular inner member lying within said outer member, said inner member having a distal end located near the distal end of the lead, said inner member extending substantially to the proximal end of the lead and defining a central lumen, at least one electrode secured to said outer member near the distal end of the lead, at least one conductor connected to said at least one electrode for transmitting electrical signals from the proximal end of the lead to said at least one electrode, a stylet for insertion in the central lumen of the lead, said stylet having an enlarged tip of predetermined shape at a distal end, and capture means connected to said flexible tubular outer member at the distal end of the lead for releasably securing in a stabilized positional relationship the enlarged tip of said stylet to the lead in a manner that prevents rotation of said lead with respect to said flexible tubular outer member, such that the lead can be positioned in a desired location by at least one of advancing and withdrawing and rotating said stylet.

2. An elongated lead having a distal end and a proximal end, the lead comprising:

a flexible tubular casing substantially concentric to a longitudinal axis of the lead, said casing extending substantially an entire length of the lead and defining a central lumen, a stylet for insertion in the central lumen of the lead, said stylet having an enlarged tip of predetermined shape at a distal end, and capture means connected to said tubular casing at the distal end of the lead for releasably securing in a stabilized positional relationship the enlarged tip of said stylet to the lead in a manner that prevents rotation of said stylet with respect to said tubular casing, such that the lead can be positioned in a desired location by at least one of advancing and withdrawing and rotating said stylet.

3. The lead of claim 2 further including at least one electrode located near the distal end and at least one conductor for transmitting electrical signals from the proximal end of the lead to said at least one electrode.

4. The lead of claim 2 wherein said capture means comprises a capture member including an aperture having a necked down portion and a socket portion, said socket portion being shaped to accommodate, the predetermined shape of the enlarged tip of said stylet.

5. An epidural lead having a distal end and a proximal end, the epidural lead comprising:

a flexible tubular outer member substantially concentric to a longitudinal axis of the lead, said outer member extending substantially an entire length of the lead, a flexible tubular inner member lying within said outer member, said inner member having a distal end located near the distal end of the lead, said inner member extending substantially to the proximal end of the lead and defining a central lumen, at least one electrode secured to said outer member near the distal end of the lead, at least one conductor connected to said at least one electrode for transmitting electrical signals of the proximal end of the lead to said at least one electrode, a stylet for insertion in the central lumen of the lead, said stylet having an enlarged tip at a distal end, and capture means connected to said flexible tubular outer member at the distal end of the lead for releasably securing in a stabilized positional relationship the enlarged tip of said stylet to the lead in a manner that prevents rotation of said stylet with respect to said flexible tubular outer member, such that the lead can be positioned in a desired location by at least one of advancing and withdrawing and rotating said stylet.

6. The lead of claim 5 wherein said capture means comprises a capture member including an aperture having a necked down portion and a socket portion, said socket portion being shaped to accommodate the predetermined shape of the enlarged tip of said stylet.

7. A method for positioning a lead in the human body, the lead having a distal end and a proximal end and including a flexible tubular casing substantially concentric to a longitudinal axis of the lead, the tubular casing extending substantially the entire length of the lead and defining a central lumen, the method comprising:

inserting a stylet in the central lumen of the lead, said stylet having an enlarged tip of predetermined shape at a distal end, securing the enlarged tip of said stylet to the distal end of the lead by releasably engaging the enlarged tip in a capture member connected to the tubular casing at the distal end of the lead in a manner that prevents rotation of said stylet with respect to the tubular casing, such that the lead can be positioned in a desired location by at least one of advancing and withdrawing and rotating said stylet.

8. The method of claim 7 wherein said capture member comprises an aperture having a necked down portion and a socket portion, said socket portion being shaped to accommodate the predetermined shape of the enlarged tip of said stylet.

* * * * *